United States Patent
Axon et al.

(10) Patent No.: US 6,204,411 B1
(45) Date of Patent: Mar. 20, 2001

(54) PROCESS FOR THE PRODUCTION OF AROMATIC AMINES

(75) Inventors: Sean Alexander Axon, Wezembeek-Oppem (BE); Samuel David Jackson, Darlington (GB); Peter Rene Rik Claes, Overpelt (BE)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/137,974

(22) Filed: Aug. 21, 1998

(30) Foreign Application Priority Data

Aug. 21, 1997 (EP) .................................. 97114495

(51) Int. Cl.$^7$ .................................. C07C 209/00
(52) U.S. Cl. .......................................... 564/408
(58) Field of Search ............................. 564/408

(56) References Cited

U.S. PATENT DOCUMENTS

| 2,948,755 | 8/1960 | Schmerling . |
|---|---|---|
| 4,031,106 | * 6/1977 | DelPesco . |

FOREIGN PATENT DOCUMENTS

293715 * 10/1994 (JP) .

* cited by examiner

*Primary Examiner*—Paul J. Killos
(74) *Attorney, Agent, or Firm*—Pillsbury Winthrop LLP

(57) ABSTRACT

Process for the production of an aromatic amine by reacting an aromatic hydrocarbon with ammonia at a temperature of less than 500° C. and a pressure of less than 10 bara in the presence of a catalyst comprising at least one metal selected from the group consisting of the transition elements, lanthanides and actinides, preferably in the presence of an oxidant.

9 Claims, 1 Drawing Sheet

PROCESS FOR THE PRODUCTION OF AROMATIC AMINES

FIELD OF THE INVENTION

Figure 1:
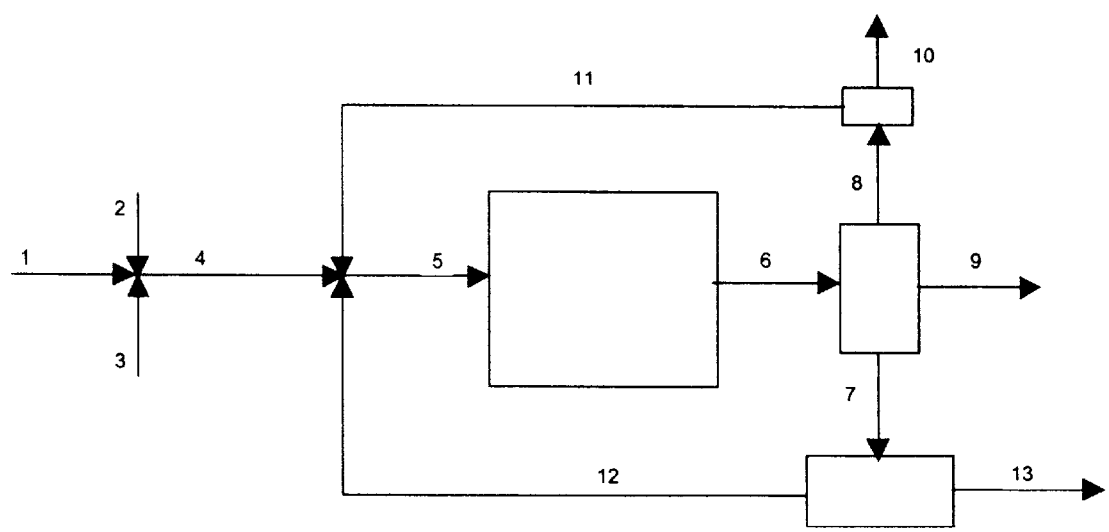

The present invention relates to a process for the production of aromatic amines, in particular aniline. More specifically, the present invention relates to an ammoxidation and/or an oxidative dehydrogenation/coupling reaction.

BACKGROUND OF THE INVENTION

Commonly used processes for the preparation of aromatic amines comprise two process stages: the aromatic hydrocarbon is first nitrated and then the nitrated aromatic hydrocarbon is hydrogenated to form the corresponding amine compound. Such processes have the drawback that they are energy and time consuming, require large amounts of reactants, and result in the production of considerable amounts of undesired by-products which need to be removed.

Accordingly there still remains a need for a process to produce aromatic amines directly from aromatic hydrocarbons resulting in a high yield and/or a substantially complete conversion.

Therefore, the present invention has the objective to provide a process for efficiently preparing aromatic amines, in particular aniline with high selectivity. A process with sufficiently high selectivity will improve the operating efficiency of the overall process by reducing the amount of unwanted end-products produced, allowing the process to be used on an industrial basis.

The process of the present invention is advantageous in its simplicity, use of operation, low capital and operating costs. The process can be run at a relatively low conversion of the feed hydrocarbon to the desired product due to the selectivity achieved. Selectivity is the amount of desired product divided by the total of all (desired and by-products) products. It will be appreciated that a process that runs at enhanced selectivity is highly advantageous even though the conversion may be low.

The selectivity achieved with the present process permits operation of the process at a relative low conversion, i.e. a change from the conventional objective of achieving the highest possible conversion. A substantial economic benefit is realised on an industrial scale even from increase in selectivity, which is achieved by the present invention, since the process retains and recycles a relative high percentage of unreacted aromatic hydrocarbon and ammonia.

The amount of unreacted aromatic hydrocarbon will depend on the percent per-pass conversion of the reactant aromatic hydrocarbon entering the ammoxidation reactor which is converted to products. Those skilled in the art will appreciate that factors such as specific choice of catalyst, specific operating temperature and the like can be adjusted to have the reactor operate at a desired conversion of the reactant aromatic hydrocarbon.

At lower operating conversion, there will be a greater amount of unreacted aromatic hydrocarbon and unreacted ammonia circulating in the process.

According to one embodiment of the present invention a process is provided for the production of aromatic amines by reacting an aromatic hydrocarbon with ammonia at a temperature of less than 500° C. and a pressure of less than 10 bara in the presence of a catalyst comprising at least one metal selected from the group consisting of the transition elements, lanthanides and actinides.

According to another embodiment of the present invention, the process of the present invention allows to recycle a high percentage of unreacted aromatic hydrocarbon and ammonia (FIG. 1).

According to a preferred embodiment of the present invention, the aromatic hydrocarbon reacts with ammonia in the presence of an oxygen-containing gas.

More direct methods for the preparation of aromatic amines from aromatic hydrocarbons have been described in the prior art.

CA-A-553988 concerns a one-step process for the production of aromatic amines. In one embodiment a mixture of benzene, ammonia and oxygen is contacted in the vapour phase with a platinum catalyst at a temperature of about 1000° C. In another embodiment, a mixture of benzene and ammonia is contacted in the vapour phase with a reducible metal oxide at a temperature of about 100 to 1000IC.

GB-A-1463997 describes a process for the amination of an aromatic compound which is miscible with ammonia comprising reacting said compound with ammonia at an elevated temperature and at a superatmospheric pressure in the presence of a doped conditioned nickel/nickel oxide/zirconium catalyst system.

In GB-A-1327494 a process is described for converting aromatic compounds and ammonia to aromatic amines in the presence of a prereduced and conditioned nickel/nickel oxide catalyst composition at a temperature in the range of 150 to 500° C. and at a pressure in the range of 10 to 1000 atmospheres.

U.S. Pat. No. 2,948,755 discloses the preparation of aromatic amines by reacting an aromatic compound such as benzene with anhydrous ammonia in the presence of a group VI-B metal compound and a promoter consisting of an easily reducible metallic oxide at a temperature in the range from about 200 to 600° C.

JP-A 06/293715 describes a process for aminating and/or cyanating an aromatic compound in the presence of ammonia using a catalyst carrying a Group VIII-element. In an example a Fe-silica catalyst is used for amination of benzene at 400° C. The conversion rate of benzene was 0.85% and the selectivity rate for aniline was 97.3%.

None of the cited prior art documents disclose the features of the present process nor do these documents suggest the benefits associated with the process of the present invention.

DETAILED DESCRIPTION OF THE INVENTION

The present invention thus provides a process for the production of aromatic amines by reacting an aromatic hydrocarbon with ammonia at a temperature of less than 500° C. and a pressure of less than 10 bara in the presence of a catalyst comprising at least one metal selected from the group consisting of the transition elements, lanthanides and actinides. Suitable aromatic hydrocarbons for use in the present invention include, for example, benzene, toluene, ethylbenzene, n-propylbenzene, isopropyl-benzene, n-butylbenzene, xylenes, diethylbenzenes, trimethylbenzene, ethyltoluene, naphthalene, anthracene, chrysene, phenanthrene and pyrene.

The preferred aromatic hydrocarbon is benzene, producing aniline in the process of the present invention.

While ammonia is preferred, it is anticipated that other amines such as methylamine may be used as the source of the amino-function substituted on the aromatic hydrocarbon.

The reaction is preferably carried out at a temperature between 300 and 450° C. and more preferably between 350 and 400° C.

It is preferred to employ pressures between 1 and 7 bara, more preferably between 2 and 5 bara. Typically an excess of ammonia over the stoichiometric amount is employed. Typically, the molar ratio of ammonia to hydrocarbon is from 1:1 to 10:1, preferably from 1:1 to 3:1.

The reaction time largely depends on the reaction conditions such as pressure and temperature, and on the type of catalyst used.

The metal used in the catalyst may be any transition element, a lanthanide or an actinide, or mixtures thereof Generally, Group I-B, IV-B, V-B, VI-B or VIII-metals are used.

The catalyst may comprise the metals in their pure form or oxides thereof Mixtures of metals with their oxides, or with oxides from other metals, are preferred for the purposes of the present invention. In accordance with the present invention, it has been found that selected catalysts, especially vanadium, when being present as oxides, enhances the selectivity.

The metals may be unsupported, for example in the form of alloys, or supported on a carrier.

Suitable carriers for supporting the metal or metal oxide include, for example, alumina, silica, aluminosilicate, carbon and other supports normally employed in supported heterogeneous catalyst systems.

Unsupported catalysts may be for example, in the form of a wire, sponge, particulate, sphere but are preferably present in the form of a wire gauze.

The catalyst may be in any suitable physical form including pellets and extrudates. The catalyst may be prepared by any method known to those skilled in the art.

Preferred are metals such as platinum, palladium, rhodium, vanadium, cobalt, copper, nickel, chromium, zirconium, silver or gold, or mixtures thereof.

Copper, platinum, vanadium, rhodium and palladium are most preferred. Platinum and vanadium are highly preferred metals for the purpose of the present invention.

The amount of catalyst used mainly depends on the type of catalyst and amount of reactants present in the reaction system.

The process of the invention is either a liquid phase or a vapour phase process which may be carried out semi-continuously or continuously. Both the reactants, the aromatic hydrocarbon and the ammonia, may be charged to the reactor as a gas or liquid. Preferred process is vapour phase.

The continuous process is carried out in, for example, a fixed bed operation, a moving bed operation, in which the reaction bed and the reactants either pass co-currently or countercurrently to each other, trickle bed or slurry type operation in which the catalyst is carried into the reactor as a slurry in the aromatic hydrocarbon.

The catalyst may be regenerated intermittently or continuously to maintain its catalytic activity at the desired level.

According to another embodiment of the present invention, it has been found that the selectivity and/ or conversion of the present process can be improved by the presence of an oxidant especially an oxygen containing gas.

The oxygen-containing gas used in the invention may be air, oxygen-enriched air, other oxygen-inert gas mixtures or substantially pure oxygen. By oxygen-enriched air is meant air that contains more oxygen than is naturally present in air. Oxygen-inert gas mixtures include oxygen-nitrogen mixtures, oxygen-argon mixtures, etc. Other suitable oxidants are oxides of nitrogen or peroxides including hydrogen peroxide.

The molar ratio of oxygen in the oxygen containing gas to hydrocarbon is suitably in the range from 0.01:1 to 0.5:1, preferably from 0.02:1 to 0.1:1, highly preferred from 0.05:1 to 0.1:1.

One embodiment of the invention is described with reference to the accompanying drawing which is a diagrammatic flowsheet of a process in accordance with the invention. (FIG. 1—Table 1).

DISCREPTION OF DRAWING

Referring to the drawing 100 l/h of benzene and 300 kmol/h of ammonia are fed into the reactor (5) with 2.5 kmol/h of oxygen in air. The reaction of this feed produces 5 kmol/h of aniline and 5 kmol/h of water. All of the oxygen fed to the reactor is consumed in the reaction.

The reactor outlet (6) contains these products and the unreacted raw materials (benzene & ammonia) from the reaction. This stream enters a separation section where the nitro-en and unreacted ammonia exit in 8, the water exits in 9, and the unreacted benzene and product aniline. exit in 7.

The ammonia/nitrogen stream (8) is sent for further separation where the nitrogen exits in and the unreacted ammonia is recycled to the reactor inlet via stream 11.

The benzene/aniline is also sent for further separation and the product aniline exits in 13 whilst the unreacted benzene is recycled back to the reactor inlet via stream 12. The ammonia and benzene recycles are combined with stream 4 to make up the reactor inlet stream (5). Stream 4 contains the fresh feeds of benzene (5 kmol/h via stream 1), ammonia (5 kmol/h via stream 2) and 2.5 kmol/h of oxygen as air (via stream 3).

The selectivity for aniline is 100%; benzene conversion is 5%; hence the yield is 5%. All aniline is taken as product and all unconverted raw materials are recycled to combined feed. All oxygen is consumed in the reactor. The stoichiometric molar ratios as used in the reactor inlet are $NH_3:C_6H_6:O_2$= 3:1:0.025. The flow rates of the various streams are shown in the following table.

TABLE 1

| Stream No. | Description | Flows (kmol/hr) | | | | | |
|---|---|---|---|---|---|---|---|
| | | Oxygen | Nitrogen | Benzene | Ammonia | Aniline | Water |
| 1 | Benzene fresh feed | 0 | 0 | 5 | 0 | 0 | 0 |
| 2 | Ammonia fresh feed | 0 | 0 | 0 | 5 | 0 | 0 |
| 3 | Air feed | 2.5 | 9.4 | 0 | 0 | 0 | 0 |
| 4 | Combined fresh feed | 2.5 | 9.4 | 5 | 5 | 0 | 0 |
| 5 | Reactor inlet | 2.5 | 9.4 | 100 | 300 | 0 | 0 |
| 6 | Reactor outlet | 0 | 9.4 | 95 | 295 | 5 | 5 |
| 7 | Benzene/Aniline stream | 0 | 0 | 95 | 0 | 5 | 0 |
| 8 | Ammonia/Nitrogen stream | 0 | 9.4 | 0 | 295 | 0 | 0 |
| 9 | Water stream | 0 | 0 | 0 | 0 | 0 | 5 |
| 10 | Nitrogen stream | 0 | 9.4 | 0 | 0 | 0 | 0 |
| 11 | Ammonia recycle | 0 | 0 | 0 | 295 | 0 | 0 |
| 12 | Benzene recycle | 0 | 0 | 95 | 0 | 0 | 0 |
| 13 | Aniline product | 0 | 0 | 0 | 0 | 5 | 0 |

The following examples are provided to illustrate the invention. It is not intended to limit the scope of this invention to the embodiments described therein.

EXAMPLES

Example 1

2.93 g of a Pt/Rh gauze (Baselok™) were placed in a fixed bed reactor. The reactor was then heated to about 400° C. and pressurised to about 7 bara with an inert gas. Benzene, ammonia and an oxygen were then put through the catalyst bed in a continuous mode, whilst the pressure was varied between 4 and 10 bara and the temperature was ranged from 375° C. to 500° C. The molar ratio of ammonia to hydrocarbon to oxidant was 3:1:0.5. After the passing through the reactor the reaction products were cooled below 10C, thus allowing the collection of the organic phase. The maximum selectivity towards aniline was about 57% w/w.

Example 2

A Pt supported catalyst was made by impregnating an alumina support (AL 3992-E™) using $H_2PtCl_6$. 2.37 g of the Pt supported on alumina catalyst was placed in a tubular fixed bed reactor. This catalyst was activated using a hydrogen in nitrogen mixture for 4 hours at a temperature of 300° C. After the activation, the reactor was purged with helium, heated to 400° C. and pressurised to 9.5 bara. At the desired temperature, a mixture of ammonia and benzene (ratio about 3:1) was fed continuously into the reactor. After the stabilisation of the mentioned flows, oxygen was introduced. The molar ratio of ammonia to hydrocarbon to oxidant was 3:1:0.5. The pressure was sustained throughout the experiment by continuously removing reaction products from the system. These obtained reaction products were cooled below 10° C. and collected as liquid samples which were analysed to assess the selectivity of the tested catalyst. After 20 hours of operation the temperature was increased to 500° C. and further samples were obtained. The maximum selectivity towards aniline was 84% w/w.

Example 3

A Pt supported catalyst was made by impregnating a silica support having a surface area of 150–200 m²/g using $H_2PtCl_6$. 1.17 g of this Pt supported on silica catalyst was placed in a fixed bed reactor and 1% w/w Pt on Silica (150–200 nm²/g). The catalyst is made by impregnation technique using $H_2PtCl_6$. This catalyst bed was then activated by passing through hydrogen at 200° C. Thereafter, the reactor was heated to about 400° C. and pressurised to about 9 bara with an inert gas. Benzene, ammonia and oxygen were then put through the catalyst bed in a continuous mode, whilst the pressure was maintained and the temperature were raised up to about 500° C. The molar ratio of ammonia to hydrocarbon to oxygen was 3:1:0.05. The reaction products were then cooled below 10° C., thus allowing the collection of the organic phase. The maximum selectivity towards aniline was about 82% w/w.

Example 4

12.68 g of a vanadium oxide on alumina catalyst was placed in a fixed bed reactor. 8% w/w vanadium expressed as vanadia on AL $_{3992}$-E™. The catalyst was made by impregnation technique using ammonium methavanadate. The reactor was heated to about 450° C. and pressurised to about 9 bara with benzene, ammonia and an oxygen. These reagents were put through the catalyst bed in a continuous mode, whilst the pressure and temperature were maintained as initially set. The molar ratio of ammonia to hydrocarbon to oxygen was 3:1:0.05. The reaction products were then cooled below 10° C., thus allowing the collection of the organic phase. Maximum selectivity towards aniline of about 71 % w/w was found.

What is claimed is:

1. A process for the production of an aromatic amine, comprising:

reacting an aromatic hydrocarbon with ammonia at a temperature of less than 500° C. and a pressure of less than 10 bars in the presence of an oxidant and a catalyst comprising at least one metal selected from the group consisting of vanadium, platinum, lanthanides and actinides.

2. Process according to claim 1, wherein the aromatic hydrocarbon is benzene.

3. Process according to claim 2 or 1 wherein the temperature is between 300 and 450° C.

4. Process according to claim 3 wherein the temperature is between 350 and 400° C.

5. Process according to claim 1 wherein the pressure is between 1 and 7 bars.

6. Process according to claim 5 wherein the pressure is between 2 and 5 bars.

7. Process according to claim 1 wherein said catalyst comprise the metals in oxide form.

8. Process according to claim 1 wherein said oxidant is an oxygen containing gas, the molar ratio of the oxygen in the oxygen containing gas to hydrocarbon being in the range from 0.01:1 to 0.5:1.

9. Process according to claim 1 wherein said process is a semi-continuous or a continuous process.

* * * * *